United States Patent [19]

Ohsuga et al.

[11] Patent Number: 4,896,675
[45] Date of Patent: Jan. 30, 1990

[54] APPARATUS FOR MONITORING DEGREE OF MENTAL TENSION

[75] Inventors: Mieko Ohsuga; Futomi Shimono, both of Hyogo, Japan

[73] Assignee: Mitsubishi Denki Kabushiki Kaisha, Tokyo, Japan

[21] Appl. No.: 311,708

[22] Filed: Feb. 16, 1989

[30] Foreign Application Priority Data

Jun. 10, 1988 [JP] Japan .................. 63-144360

[51] Int. Cl.$^4$ .............................. A61B 5/02
[52] U.S. Cl. .................... 128/671; 128/905; 128/700; 128/702
[58] Field of Search .............. 128/671, 670, 905, 668, 128/700, 702, 703, 704, 708

[56] References Cited

U.S. PATENT DOCUMENTS

| | | | |
|---|---|---|---|
| 4,510,944 | 4/1985 | Porges .................. | 128/671 |
| 4,549,552 | 10/1985 | Groch et al. .......... | 128/700 |
| 4,727,882 | 3/1988 | Schneider et al. ..... | 128/671 |

OTHER PUBLICATIONS

"Respiratory Sinus Arrythmia in Humans: How Breathing Pattern Modulates Heart Rate", by Judith Ann Hirsch and Beverly Bishop: American Journal of Physiology 241, pp. 620-629, 1981.
"Respiratory Sinus Arrythmia as an Index of Parasympathetic Cardiac Control During Active Coping", by Paul Grossman and Sven Svebak: Psychophysiology, vol. 24, no. 2, pp. 228-235, 1987.
"Development of RRV Measuring Unit with LCD", by Yoshiyuki Nakagaki, Michitaka Hirose and Takemocchi Ishii, 2nd Symposium on Human Interface, pp. 119-122, Oct. 29-30, 1986.
Japanese Patent Publication (KOKOKU), no. 61-43056, Date of Publication, Sep. 25, 1986, under Application no. 53-152718, Date of Application, Dec. 12, 1978, Applicant & Inventor, Iwao Saito, Entitled "Heartbeat Bio Feedback Apparatus".
Japanese Patent Publication (KOKAI), no. 61-272034, Date of Publication, Dec. 2, 1986, under Application no. 60-113474, Date of Application, May 27, 1985, Applicant, Mitsubishi Denki Kabushiki Kaisha, Inventor Hideaki Yoshioka, Entitled "Apparatus for Measuring Respiratory Circulating Function".

Primary Examiner—Francis Jaworski
Assistant Examiner—George Manuel
Attorney, Agent, or Firm—Wolf, Greenfield & Sacks

[57] ABSTRACT

An apparatus for monitoring mental tension comprises a first measuring unit for measuring a periodic wave related to a contraction activity of the heart of a person to be monitored; a detecting unit for detecting special waves which periodically appear in the periodic wave measured by the first measuring unit; a second measuring unit for measuring the interval at which the special wave are generated; a first processor for providing, as tension index values, a mean value of an interval train of the special waves and the magnitude of a respiration component of the fluctuation of the interval train; and a display unit for displaying the resulting tension index values.

3 Claims, 8 Drawing Sheets

APPARATUS FOR MONITORING DEGREE OF MENTAL TENSION

BACKGROUND OF THE INVENTION

1. Field of the Invention

The present invention relates to an apparatus for monitoring the degree of mental tension experienced by a person which is used to check the severity of mental tension or to allow a person to train himself to promptly control the degree of tension he experiences during such pursuits as sports, giving lectures, taking examinations and so on, in which person's performance is greatly influenced by the level of mental tension.

2. Related Background Art

Figure 1:
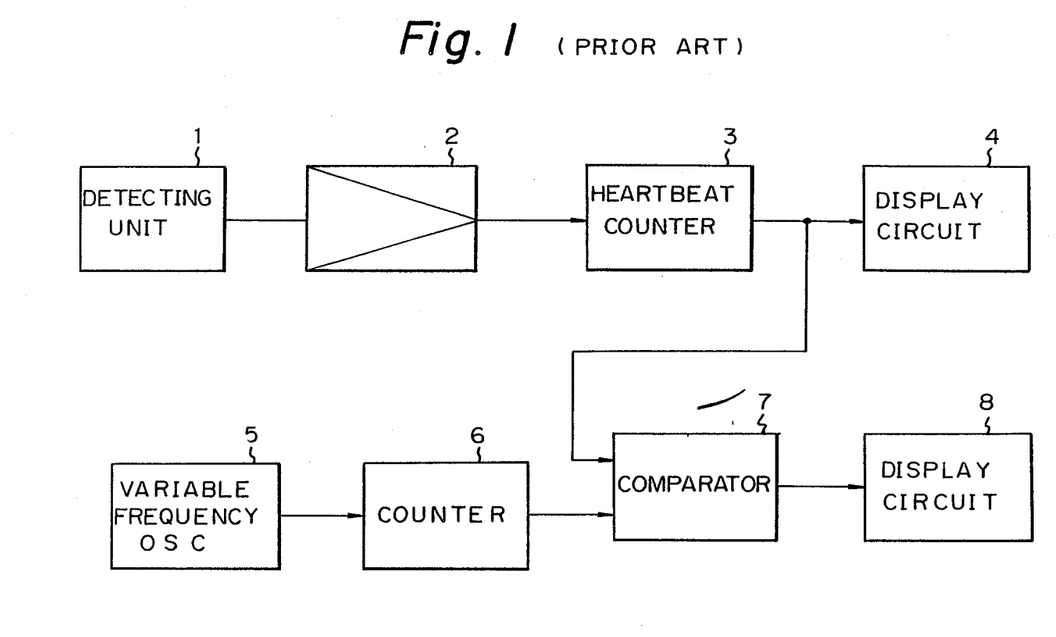
FIG. 1 is a block diagram showing a conventional apparatus adapted to monitor a heart rate.

Hitherto, many apparatuses which are adapted to monitor the heartbeat (instantaneous heartbeat or mean heartbeat over a predetermined period of time) are designed to measure a load caused by motion. One type of apparatus that is adapted to evaluate and train the automatic nerve function is known as a heartbeat bio feedback and was disclosed in JP-B-61-43056. FIG. 1 shows a schematic block diagram of such an apparatus. In the diagram, reference numeral 1 denotes a pulse wave detecting unit; 2 indicates an amplifier; 3 a heartbeat (sphygmus, pulse) counter; 4 a display circuit; 5 a variable frequency oscillator; 6 a counter; 7 a comparator; and 8 a display circuit.

The pulse wave detected by the detecting unit 1 is amplified by the amplifier 2. The pulse waves are counted by the counter 3 over a predetermined period of time and then the count value is displayed by the display circuit 4. On the other hand, pulses corresponding to the objective heart rate are generated by the variable frequency oscillator 5. The same number of pulses as the count value incremented on the counter 3 are counted over a predetermined period of time by the counter 6. The objective heart rate and the actual pulse frequency, which is output from the counter 3, are compared by the comparator 7. The result of this comparison is then displayed by the display 8.

Figure 2:
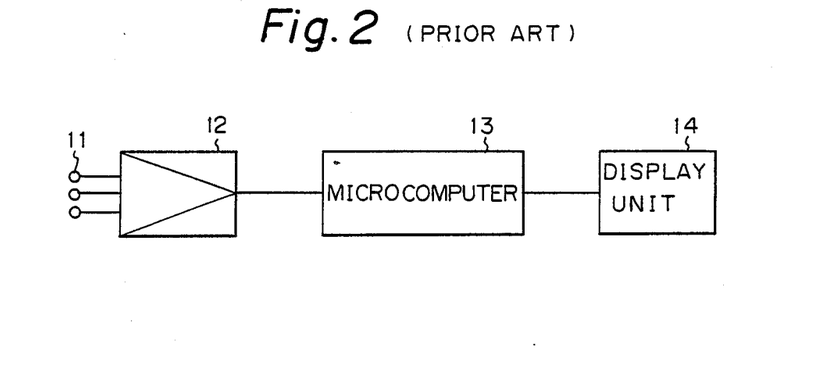
FIG. 2 is a block diagram showing a conventional RRV monitor apparatus.
Figure 3:
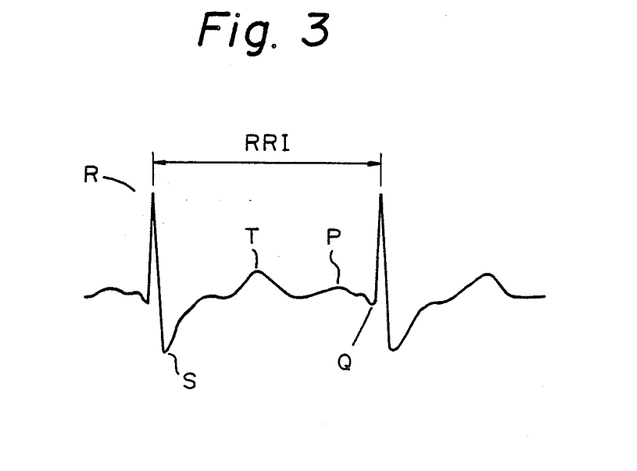
FIG. 3 is a waveform diagram showing an electrocardiogram.

On the other hand, an RRV (RR interval fluctuation) monitoring apparatus has been developed to evaluate mental loads experienced in conducting computer-related work and the like (refer to an excerpt from the 2nd Symposium on "Human Interface", pages 119 to 122, 1986). As shown in FIG. 2, the monitoring apparatus comprises sensors 11, an amplifier 12, a microcomputer 13 and a display unit 14. FIG. 3 shows an electrocardiogram. In the diagram, P, Q, R, S and T represent P wave, Q wave, R wave, S wave and T wave, respectively, and RRI (R-R Interval) indicates the time interval between two R waves. In the apparatus shown in FIG. 2, the electrocardiogram can be obtained through the sensors 11 and the amplifier 12. Next, in the microcomputer section 13, the R wave in the electrocardiogram is detected to obtain the RRI which is then converted into the interval data at regular intervals. Then a variance (corresponding to the square of the standard deviation SD) is calculated and displayed by the display unit 14. Another known example of such an apparatus is the apparatus for measuring the respiratory circulating function disclosed in JP-A-61-272034.

Since only the heart rate is displayed in the conventional heart rate monitor, there is a problem in that any physiological change in the heartbeat due to changes in motion, posture, respiration pattern and the like cannot be differentiated mental tension; hence any change in mental tension degree cannot be accurately monitored. On the other hand, the RRV monitor also has a similar problem because all of the fluctuation components are lumped together to be evaluated.

SUMMARY OF THE INVENTION

It is the first object of the present invention to provide an apparatus for monitoring mental tension in which any change in the degree of mental tension can be accurately monitored in regard to various aspects.

In addition to the first object, another object of the invention is to provide an apparatus for monitoring mental tension which evaluates the reliability of an index value indicative of the measured degree of tension.

Still another object of the invention is to provide an apparatus for monitoring mental tension which raises the reliability of an index value indicative of the measured degree of tension.

Still another object of the invention is to provide an apparatus for monitoring mental tension comprising: a first measuring unit for measuring a periodic wave related to the contraction activity of the heart of a person to be monitored; a detecting unit for detecting a special wave which periodically appears in the periodic wave measured by the first measuring unit; a second measuring unit for measuring the interval at which the special waves are generated; a first processor for calculating a mean value of the interval train of the special waves and the magnitude of the respiration component of the fluctuation of the interval train, and for providing a tension index value; and a display unit for displaying the tension index value.

Still another object of the invention is to provide an apparatus for monitoring mental tension which includes a second processor for obtaining, as a reliability evaluation value of a tension index value, at least one of the frequency of the respiration component of the fluctuation and the magnitude of the low frequency component of the fluctuation of the interval train; and an output unit for outputting the reliability evaluation value.

Still another object of the invention is to provide an apparatus for monitoring mental tension which includes a unit for stabilizing the respiration of a person to be monitored, so that the reliability of the tension index value is raised.

In an apparatus for monitoring mental tension according to the present invention, both (1) the mean value of the interval train of the special wave in the periodic wave (for instance, cardiac wave) originated from the contraction activity of the heart, and (2) the magnitude of the respiration component of the fluctuation of the interval train are used as index values representing the degree of mental tension, so that the mental tension can be monitored from different two perspectives. Although the details of the physiological mechanism behind the relationship between each of the two indices and the degree of mental tension have not yet been clarified, it is generally known that when mental tension rises, both of these indices decrease. In addition, it is known that the two indices related to different kinds of mental tension and thus that the former index is antagonistically dominated by the sympathetic nervous system and parasympathetic nervous system, while the latter is mainly and more strongly dominated by the parasympathetic nervous system. By using the two indices, therefore, any change in mental tension can be more accurately monitored than with the conventional monitors.

Also, in an apparatus for monitoring mental tension according to the invention, the operation performed by the second processor for obtaining an evaluation of the reliability is also integrated. Since the two tension index values vary greatly with changes in a respiration pattern, the respiration pattern needs to be controlled at the same time as monitoring mental tension is being performed. In order to check whether or not the respiration pattern is being accurately controlled in other words, whether or not the monitored index values are reliable, the frequency of the respiration component of the fluctuation of the interval train of special waves is obtained and output as a reliability evaluation value. The state of control of the respiration pattern can be checked on the basis of the frequency of the respiration component. In addition, the reliability of the tension index value can be evaluated by the magnitude of the low frequency component of the fluctuation of the interval train due to an abrupt big and slow respiration, physical motion or the like, in a manner similar to the above. Therefore, mental tension can be monitored with high reliability by evaluating the reliability of the tension index value on the basis of at least one of the frequency of the respiration component and the magnitude of the low frequency component.

In an apparatus for monitoring mental tension according to the invention, the operation conducted by the respiration stabilizing unit is integrated too. In this respiration stabilizing unit, a sound such as a rhythm or melody is generated during measurement or a desirable respiration pattern is visually displayed as a graph. The measurement that takes place under a stable respiration condition can be based on having the person to be monitored breath in harmony with such a sound or respiration pattern. This method which utilizes a rhythm or melody also offers the advantage that the respiration of the person to be monitored can be encouraged to assume a desired state by suitably selecting the type of rhythm or melody in accordance with the desired objective. This means that the reliability of an apparatus for monitoring mental tension can be further improved by adopting such a method.

DETAILED DESCRIPTION OF PREFERRED EMBODIMENTS

Figure 4:
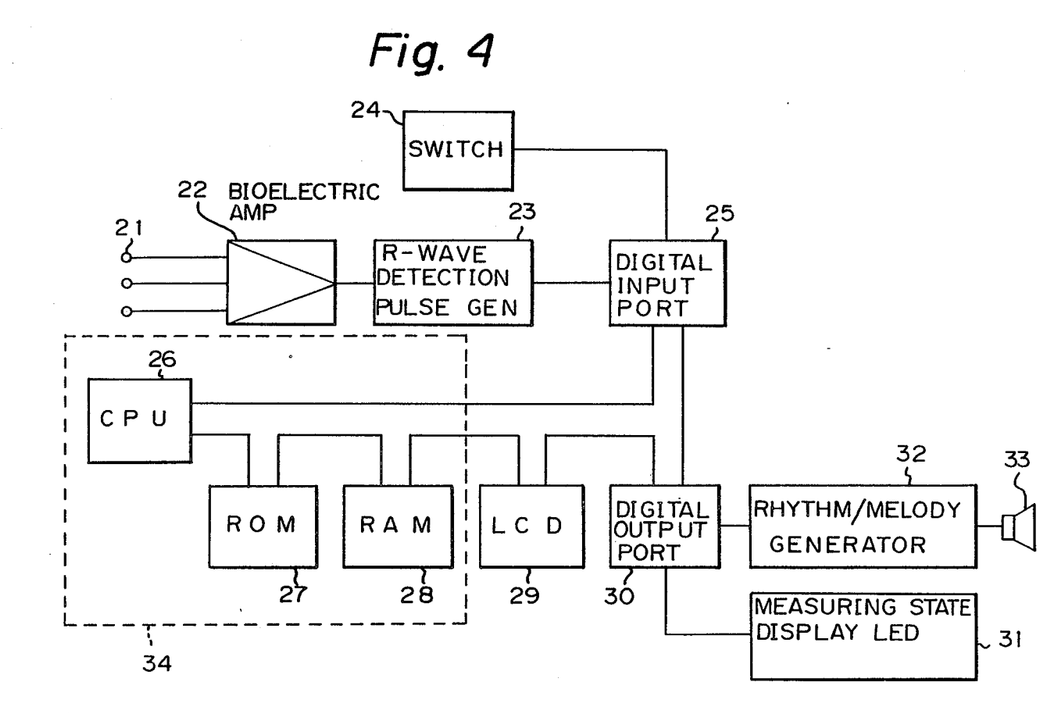
FIG. 4 is a block diagram showing an apparatus for monitoring mental tension according to an embodiment of the present invention.

An embodiment of the present invention will be described below with reference to the drawings. In the embodiment, as an example, a cardiogram waveform is measured as a periodic wave originated from the contraction activity of the heart. In FIG. 4, reference numeral 21 denotes cardiogram detecting electrodes attached to the body of a person to be measured; 22 indicates an bioelectric amplifier; 23 a cardiogram R-wave detector and pulse generator; 24 a switch adapted to start the measurement; 25 a digital input port adapted to input an R-wave detection pulse and a measurement start signal; 26 a CPU (central processing unit) of a microcomputer adapted to obtain tension index values and to control the display of such index values; 27 an ROM (Read Only Memory) adapted to store a program; 28 an RAM (Random Access Memory) adapted to store measured data and data for display; 29 a liquid crystal display (hereinafter, simply referred to as an LCD) adapted to display index values; 30 a digital output port adapted to output a measuring state signal and a signal for starting or finishing the generation of a rhythm or melody; 31 an LED (Light Emitting Diode) adapted to display the state of measurement; 32 a rhythm/melody generator; 33 a speaker or earphones; and 34 a microcomputer comprising the CPU 26, ROM 27 and RAM 28.

The electrodes 21 and the bioelectric amplifier 22 provide a first measuring port for measuring a cardiogram waveform. The pulse generator 23 and the digital input port 25 provide a detecting unit for detecting a special wave which periodically appears in the cardiogram waveform, in this case, an R wave as shown in FIG. 3. In accordance with, for example, the flowchart shown in FIG. 5, the microcomputer 34 provides a second measuring unit for measuring the interval at which the R waves are generated, a first processor for obtaining values of a tension index and a second processor for obtaining an evaluation value of the reliability of the latter, and controls output of the tension index values and reliability evaluation value and, further, controls the operation of a respiration stabilizing unit. In the embodiment, the respiration stabilizing unit is used to stabilize respiration by generating a rhythm or melody and utilizes the rhythm/melody generator 32 and the speaker or earphones 33. The tension index values and the reliability evaluation value are displayed by the LCD 29.

Figure 5:
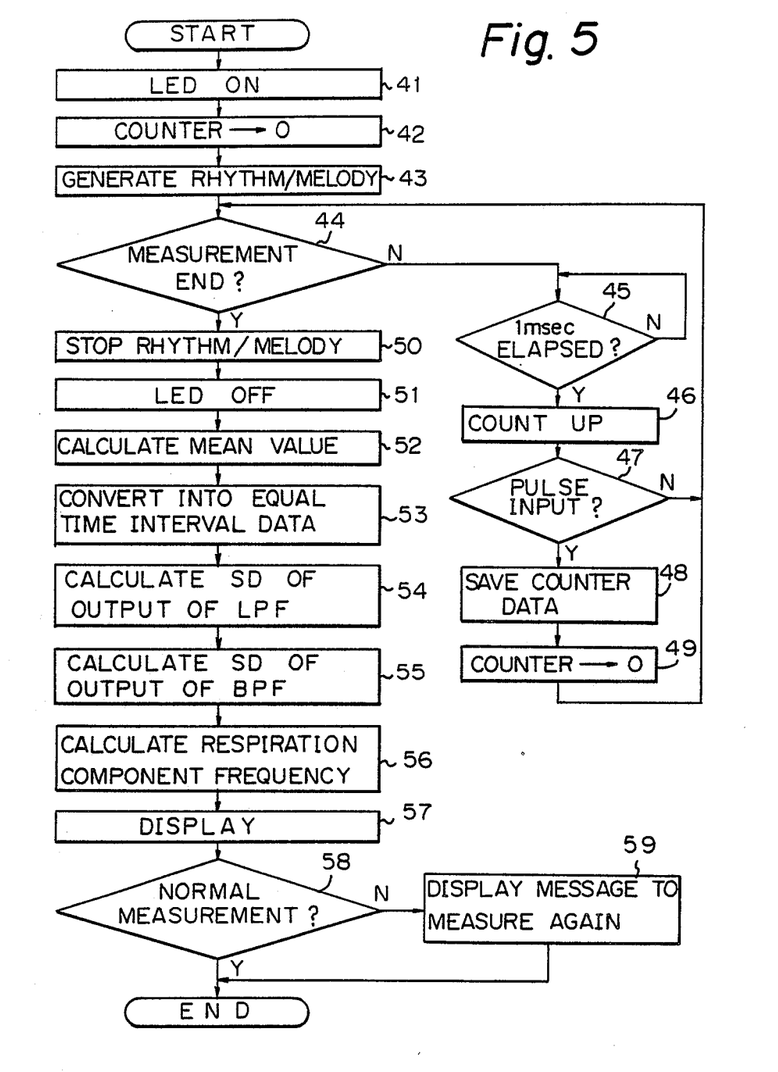
FIG. 5 is a flowchart showing the operation of a microcomputer in accordance with an embodiment of the invention.

The operation of the apparatus shown in FIG. 4 will be described below with reference to the flowchart of FIG. 5. In the microcomputer 34, the interval of R-wave detection pulses is measured, tension index values are determined, and display data is formed. The measurement operation is started by operating the start switch 24 and then is executed for preset time T. The time T is determined by adding a given time period ($t_a$: about 10 seconds) in consideration of both (i) the possibility of a mixture of noises being produced at the start of the measurement operation (i.e., influence due to disturbance of the respiration before the measurement operation is started and influence due to depression of the switch) and (ii) the delay time of a digital filter provided in the apparatus, to a given time period ($t_m$: about 20 seconds) which is used in the actual monitoring operation. When the measurement operation is started, the measuring state display LED 31 is simultaneously turned on (step 41). A counter is reset to zero for initialization (step 42). The rhythm/melody generator 32 is made operative through the digital output port 30, thereby generating a rhythm or melody which is output through the speaker or earphones 33 (step 43). The pitch of the rhythm or melody is set to a suitable value to allow the person to breath in harmony with a desired respiratory frequency $F_r$. The value of frequency $F_r$ differs depending on the type of exercise and the objective and is generally set to a frequency within the range of from about 0.1 to 0.4 Hz. In the case of training to relax, the frequency $F_r$ is set to a value which is slightly slower than ordinary respiration. It can also be set to a frequency which is slightly faster than ordinary respiration in order to raise the tension level. For instance, in the case of three-part breathing or simple triple time, a respiration pattern is matched with the rhythm or melody in such a manner that the subject inhales three times and then exhales three times. In the case of relaxation training, it is possible to adapt a respiration pattern based on a breath adjusting method of inhaling twice and then exhaling four times. However, in order to realize a consistent monitoring operation, it is necessary that respirations follow the same pattern and speed during a given measurement operation. Measurement of the cardiogram waveform with the electrodes 21 attached to the person to be monitored and bioelectric amplifier 22 is started simultaneously with the start of the generation of the rhythm or melody or before such generation, and the measured waveform is applied to the R-wave detector and pulse generator 23 so as to be converted into a pulse corresponding to the R wave, and this pulse is applied to the microcomputer 34 through the digital input port 25.

Figure 6A:
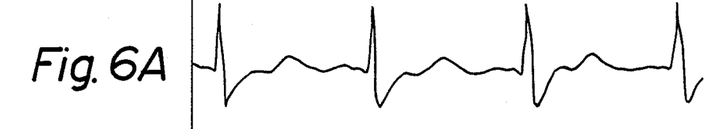
FIGS. 6A to 6D and 7A to 7C are waveform diagrams illustrating processing procedures according to an embodiment of the invention.
Figure 6B:
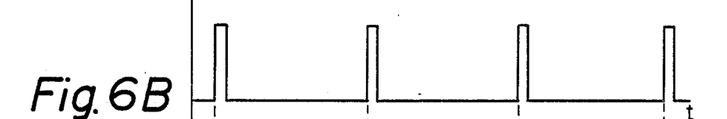
Figure 6C:
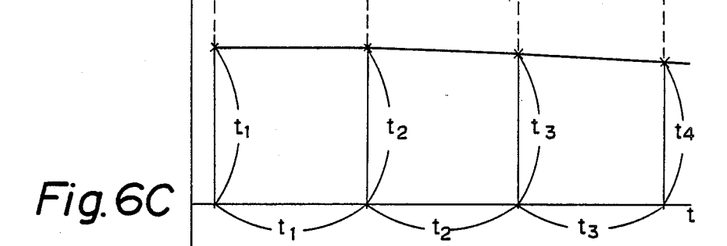

In the microcomputer 34, tension index values and a reliability evaluation value are ca;culated from the input R-wave pulse. FIGS. 6A to 6D and 7A to 7C are waveform diagrams illustrating the processes followed in obtaining these values from the cardiogram waveform. FIG. 6A shows a cardiogram waveform which is detected by the electrodes 21 and is amplified by the amplifier 22. FIG. 6B shows a pulse waveform which is obtained by applying the waveform shown in FIG. 6A to the pulse generator 23 and which is applied to the microcomputer 34. The pulse waveform is actually input as digital values into the microcomputer 34. The microcomputer 34 determines whether or not the measurement operation has been executed during the time T set in step 44. If the measuring time falls within T, the apparatus is set to the waiting mode for the duration of first one msec (step 45). This waiting process allows the measurement operation to be executed once every millisecond. Each time one msec elapses, the counter counts up the count value (step 46). A check is then made to see if the R-wave detection pulse has been input from the digital input port 25 during one millisecond (step 47). If YES, the counter data corresponding to the data indicative of the generation intervals $t_1, t_2, \ldots$ shown in FIG. 6C is saved as RR (between two R waves) interval data (step 48). Then the counter is reset to 0 (step 49). If no pulse is input in step 47, the processing routine is returned to step 44 and the RR interval data train is collected until the set time T for measuring has elapsed. If the set time T has elapsed in step 44, the generation of the rhythm or melody is stopped (step 50). Then, the measuring state display LED is turned off (step 51). Thus, the operation of measuring the generation interval train of the R waves is finished.

Figure 6D:
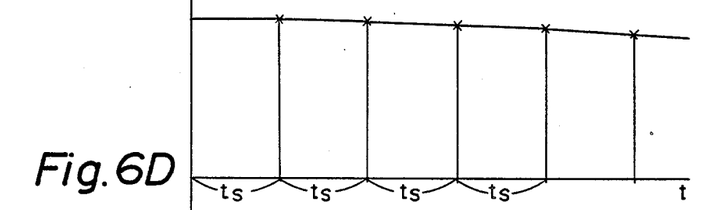
Figure 7A:
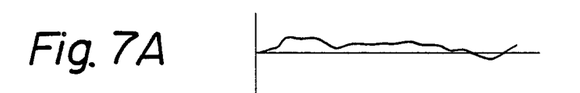
Figure 7B:
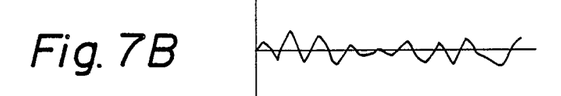
Figure 7C:
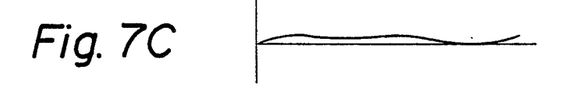

The operation for obtaining the tension index values and the reliability evaluation value will now be described. The mean value of the RR interval train which has been saved in step 48 (hereinafter, referred to as an RR mean value) is calculated (step 52). The data train relates to the data which is obtained during last $t_m$ seconds before completion of the measurement operation. Next, the RR interval train shown in FIG. 6C is converted into equal time interval data for a sampling interval $t_s$ ($t_s$ is set to about 0.5 second) as shown in FIG. 6D (step 53). A waveform as shown in FIG. 7A can be obtained by enlarging the scale of a time base as an axis of abscissa of the equal time interval data shown in FIG. 6D. The waveform of the equal time interval data includes both a respiration component of the fluctuation shown in FIG. 7B and a low frequency component shown in FIG. 7C. Therefore, when the equal time interval data (FIG. 7A) is transmitted through a low pass filter, the low frequency component shown in FIG. 7C is output. At this time, a high-cut frequency of the low pass filter is set to about 0.1 Hz. However, in order to satisfactorily eliminate the frequency component of a preset respiration, the high-cut frequency is set to be lower than a desired respiration frequency $F_r$. A standard deviation SD is calculated from the data during the last $t_m$ seconds (the number of the data; $t_m/t_s$) which is a part of the output data from the low pass filter, and is given as the magnitude of the low frequency component of the fluctuation (hereinafter, this magnitude is referred to as a low frequency component value) (step 54). On the other hand, the respiration component shown in FIG. 7B is output by transmitting the equal time interval data (FIG. 7A) through a band pass filter. The center frequency of the band pass filter is given by $F_r$ and the band pass is given by about 0.1 Hz. Thus, the standard deviation SD of the data (during the last $t_m$ seconds in FIG. 7C) indicative of the magnitude of the respiration component of the fluctuation which is output from the band pass filter is calcuated (step 55). The resultant SD is given as the magnitude of the respiration component of the fluctuation (hereinafter, such a magnitude is referred to as a respiration component value). On the other hand, the peaks (or valleys) of the data train of the respiration components shown in FIG. 7B are detected and the frequency of the respiration component of the fluctuation (hereinafter, referred to as a respiration component frequency) is obtained from the number of peaks (or valleys) and the duration of the generation of the peaks (step 56).

The respiration component frequency can be calculated by, for instance, the following equation.

Respiration component frequency $= N/t_m$

N: the number of peaks (or valleys) of the data train of the respiration components within the measuring time $t_m$ $t_m$: measuring time The RR mean value obtained in step 52 and the respiration component value obtained in step 55 are given as tension index values. The low frequency component value obtained in step 54 and the respiration component frequency obtained in step 56 are given as reliability evaluation values. The tension index values and the reliability evaluation values are displayed on the LCD 29 (step 57).

Figure 8:
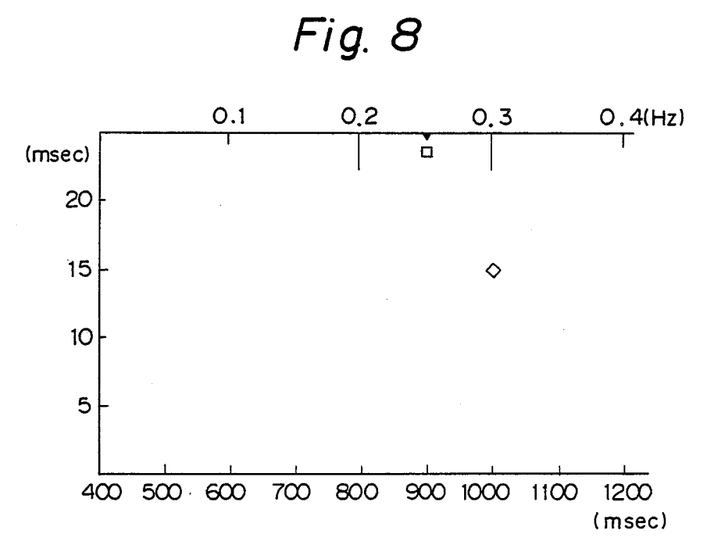
FIGS. 8 and 9 are graphs showing examples of display according to an embodiment of the invention.

An example of how the tension index values and the reliability evaluation values are displayed on the LCD 29 is shown in FIG. 8.

In the diagram, the axis of abscissa denotes the RR mean value (1000 msec in the example) and the axis of ordinate indicates the respiration component value (15 msec in the example) and these values are plotted as "◇". A check is made to see if the low frequency component value is larger than a set value (e.g., about 20 msec) or smaller (step 58). The result of this check is displayed by a different plotting mark. For instance, when the low frequency component value exceeds the set value, "X" is displayed. The respiration component frequency is plotted as "□" on the scale of the axis of abscissa on the graph. A desirable respiration frequency "▼" and range of tolerance "| |" are also displayed. When the values are out of the range of tolerance and when the low frequency component value is larger than the set value (that is, when "x" is plotted), a message prompted the subject to reexecute the measurement operation is displayed (step 59). After completion of the display (step 57 and 59), the monitoring process is finished.

Figure 9:
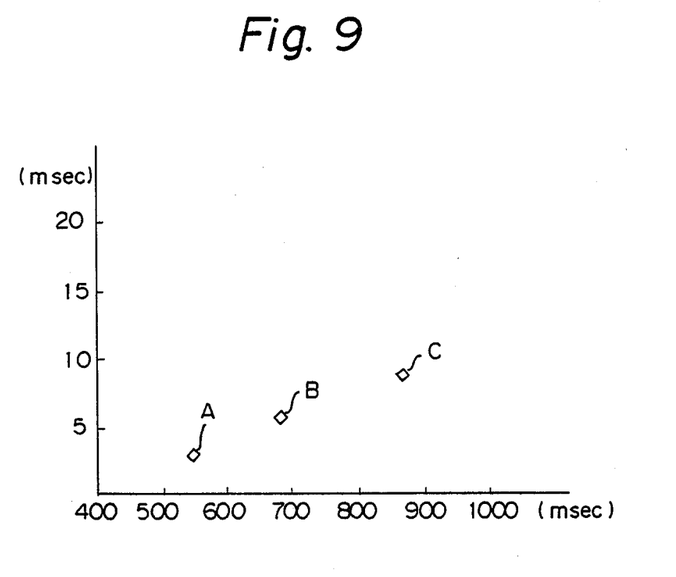

FIG. 9 shows another example of a display on the LCD 29 according to an embodiment of the present invention. Plot A shows the result of measurement in a case where the degree of tension being experienced by the person being monitored is very high, plot B shows a case of moderate tension, and plot C shows a case where the person is relaxed. As seen with these results, when the plot is located in the right upper portion of the graph, the subject is in the relaxed state. When the plot is located in the left lower portion, a high degree of tension is indicated. As will be obvious from the results, if both the RR mean value and the respiration component value are displayed as tension index values, the degree of tension of a person to be monitored can be monitored relatively accurately. Further, such a monitor can be effectively used to find out the optimum level of tension for an individual in relation to a given task or exercise.

In the embodiment, the process up to the generation of the R-wave detection pulses is performed by utilizing hardware circuit, and the process following the interval measurement is performed by utilizing microcomputer software. However, these operations can be performed by utilizing either hardware or software alone. The display device is not limited to the LCD panel, exemplified, and a LED display, CRT, EL (Electro Luminescence) display, or the like can also be used.

In the above embodiment, the method of displaying the tension index values is one in which two index values are plotted as x and y on a two-dimensional graph and the marks are changed and displayed as reliability evaluation values on the basis of the magnitude of the low frequency component value. However, the necessary tension index values and reliability evaluation values can also be displayed as numerical values, bar graphs, or the like, respectively. It is also possible to just display the result of the judgement as to whether the respiration component frequency lies within a preset range or not. It is also possible to display the result of a judgement as to whether the condition of the low frequency component value being a set value or less and the condition of the respiration component frequency lying within a set range are both satisfied, or to merely output such a result as a sound or the like. The respiration component value and the low frequency component value have been utilized by making the SD value of the filter output correspond to the effective value. However, the invention is not limited to such an effective value. A peak-to-peak value or a power value can be used instead. These components can also be extracted by spectrum analysis using an FET (high speed Fourier transformation) or AR (autoregression) model without using a filter. Also, when the apparatus is used for training, objective ranges of the RR mean value and respiration component value may be displayed, and the training may be executed within the objective ranges. There is an advantage in such a case in that the apparatus is very useful for self control training aimed at achieving an optimum condition.

In the above embodiment, the example of using the interval between the R waves of the cardiogram is adapted. However, in place of detecting the R waves, P, Q, S or T waves can be detected if a suitable period on the cardiogram can be measured. In place of measuring the cardiogram, another periodic wave regarding the contraction activity of the heart, that is a pulse wave, heart sound, or the like may be measured and then the interval between special waves which periodically appear in the periodic wave may be used in place of the interval between R waves.

Figure 10A:
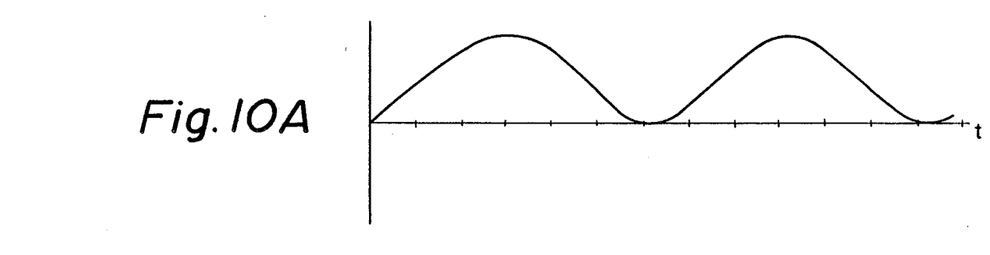
FIGS. 10A and 10B are graphs showing examples of display of respiration pattern waveforms according to another embodiment of the invention.
Figure 10B:
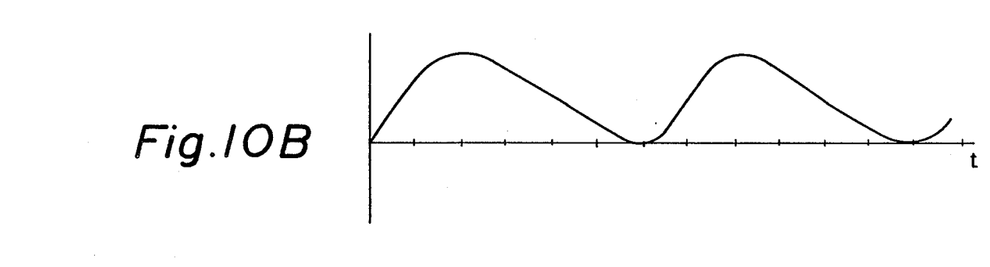

A similar effect can also be obtained by using a flickering light in place of generating a rhythm or melody for the respiration control. In FIG. 10A and 10B, the axis of abscissa represents a time base and examples of respiration patterns are shown. A person to be monitored can be instructed to breath in harmony with these respiration patterns. That is, the person is told to inhale in the rising portion of the pattern and to exhale in the falling portion. FIG. 10A shows an example of a respiration pattern which involves inhaling three times and then exhaling three times. FIG. 10B shows an example of a respiration pattern involving inhaling twice and then exhaling four times.

What is claimed is:

1. An apparatus for monitoring mental tension, comprising:
   first measuring means for measuring a periodic wave related to a contraction activity of the heart of a person to be monitored;
   detecting means for detecting special waves which periodically appear in said periodic wave measured by said first measuring means;
   second measuring means for measuring an interval at which said special waves are generated;
   first processing means for providing as tension index values, a mean value of an interval train of said special waves and magnitude of a respiration component of fluctuation of said interval train; and
   display means for displaying said tension index values.

2. An apparatus according to claim 1, further comprising:
   second processing means for providing at least one frequency of respiration component of said fluctuation and the magnitude of a low frequency component of the fluctuation of said interval train as a reliability evaluation value for evaluating reliability of said tension index values; and
   output means for outputting said reliability evaluation value.

3. An apparatus according to claim 1 or 2, further having respiration stabilizing means for stabilizing the respiration of the person being monitored, thereby raising the reliability of said tension index values.

* * * * *